United States Patent [19]

Folkers

[11] 4,110,321
[45] Aug. 29, 1978

[54] SYNTHETIC TRIDECAPEPTIDE [Gln⁴]-NEUROTENSIN HAVING HORMONAL ACTIVITY

[76] Inventor: Karl A. Folkers, 6406 Mesa Dr., Austin, Tex. 78746

[21] Appl. No.: 785,208

[22] Filed: Apr. 6, 1977

Related U.S. Application Data

[63] Continuation-in-part of Ser. No. 704,309, Jul. 12, 1976, abandoned.

[51] Int. Cl.$^2$ .......................................... C07C 103/52
[52] U.S. Cl. .............................. 260/112.5 R; 424/177
[58] Field of Search .................................. 260/112.5 R

[56] References Cited

PUBLICATIONS

R. Carraway et al., The Journal of Biological Chemistry 250, 1975, pp. 1907–1908.
R. Carraway et al., The Journal of Biological Chemistry 248, 1973, pp. 6854–6861.

*Primary Examiner*—Delbert R. Phillips
*Attorney, Agent, or Firm*—Salvatore C. Mitri

[57] ABSTRACT

A tridecapeptide, [Gln⁴]-neurotensin, has been effectively synthesized and which has the sequence (pyro)-glutamyl-leucyl-tyrosyl-glutaminyl-asparaginyl-lysyl-prolyl-arginyl-arginyl-prolyl-tyrosinyl-isoleucyl-leucyl-acid. [Gln⁴]-neurotensin has the unique hormonal activities and chemical structure of the native hormone in bovine hypothalamic tissue.

1 Claim, No Drawings

SYNTHETIC TRIDECAPEPTIDE [Gln⁴]-NEUROTENSIN HAVING HORMONAL ACTIVITY

This application is a continuation-in-part application of prior application Ser. No. 704,309 filed July 12, 1976, now abandoned.

This invention relates to a new, synthetically produced peptide which is pyroglutamyl-leucyl-tyrosinyl-glutamyl-asparaginyl-lysyl-prolyl-arginyl-arginyl-prolyl-tyrosyl-isoleucyl-leucyl-acid, and which is also designated [Gln⁴]-neurotensin. The synthetic [Gln⁴]-neurotensin has the remarkably potent and unique activities of the native hormone. More particularly, this invention relates to a process for a straightforward and economical method to synthesize a highly biologically effective and useful peptide of mammalian tissue.

BACKGROUND OF THE INVENTION

This isolation of a new hypotensive peptide, neurotensin, from bovine hypothalami was described by Carraway and Leeman (J. Biochem. 248, 6854–6861 (1973)). These investigators utilized batches of frozen hypothalamic tissue representing 2,000–4,500 animals (cows) weighing a total of 20–45 kg. The tissue was homogenized to a uniform consistency with an equal volume of $-20°$ acetone 1 N-CHl (100:3 v/v) in a colloid mill. Elaboration of this initial step and final removal of acetone yielded an aqueous residue which was lyophilized. These initial steps were performed on a preparative scale.

Purification utilizing chromatography on a G-25 Sephadex follows. Material from a bioassayed active region was pooled, lyophilized, and then taken up in 0.1 M acetic acid (100 ml/20 kg of hypothalami) and rechromatographed on a 5-liter column kept at room temperature. Again, the active region was pooled and lyophilized. Cation exchange chromatography was next utilized for further purification.

Next, preparative paper electrophoresis was utilized. The active material from 45 kg of hypothalami was applied to a 10-cm band to Whatman No. 3 MM paper and subjected to electrophoresis. Fifty percent of the active peptide was recovered from this electrophoresis and found to be a pure peptide.

By the above steps, the extracted peptide was purified approximately 200,000-fold, and approximately 3–5 nmoles of pure neurotensin was obtained/kg of wet tissue.

This isolated neurotensin from bovine hypothalami induced hypotensin in the rat and stimulated the contraction of guinea pig ileum and rat uterus. It produced relaxation of the rat duodenum. These pharmacological properties classified neurotensin as a "kinin". Its chemical composition distinguished it from any known peptide.

Subsequent to the above described isolation of neurotensin, its amino acid sequence was established by the report of Carraway and Leeman (J. Biochem. 250, 1907–1911 (1975)). The established sequence is that of pGlu-Leu-Tyr-Glu-Asn-Lys-Pro-Arg-Arg-Pro-Tyr-Ile-Leu-OH.

(The nomenclature and symbols used in expressing this sequence follow the recommendations of the IUPAC-IUB Commission of Biochemical Nomenclature (J. Biochem. 247, 977 (1972)). The results of enzymic hydrolyses and the specificities of the enzymes used to establish this sequence of neurotensin indicated that all of the amino acids are unsubstituted and are of the L-configuration.

Neurotensin was synthesized by Carraway and Leeman (J. Biochem. 250, 1912 (1975)) provided by a manual solid-phase method by a procedure which is different from the synthetic methodology used for the invention described herein. In their synthesis of neurotensin Carraway and Leeman had as their primary synethetic goal the synthesis of Gln¹ neurotensin which was then treated by heat and acid to cyclize the Gln¹-moiety to the pGlu¹-moiety or to neurotensin. In this procedure, their protected peptide was cleaved from the resin using hydrogen bromide and trifluoracetic acid. Subsequent catalytic hydrogenation removed the nitro groups from the two nitroarginyl residues before cyclization of the Gln¹-moiety to the pGlu¹-moiety.

THE INVENTION

It has now been discovered, in accordance with the present invention, that [Gln⁴]-neurotensin, can be synthesized directly by the automatic solid-phase method in which the pGlu¹-moiety is directly introduced in the last cycle of the synthesis. Deprotection and cleavage of the tridecapeptide from the resin is accomplished in one step using hydrogen fluoride to yield [Gln⁴]-neurotensin.

To achieve [Gln⁴]-neurotensin, the corresponding chain is made in the automatic total phase synthesis.

In accordance with the present invention, the tridecapeptide, [Gln⁴]-neurotensin, was synthesized as follows.

EXAMPLE

Pure L-isomers of the amino acid derivatives, purchased from Beckman, Inc., Palo Alto, California and Bachem Inc., Marina del Rey, California were used as starting materials. The amino acid analyses were carried out on a Beckman Amino Acid Analyzer, Model 119, after hydrolysis of the samples in 6N HCl overnight in evacuated sealed tubes at 130° C. The syntheses were carried out by the Merrifield solid phase procedure, in general, and with a Beckman Model 990 automatic peptide synthesizer. The α-amino groups were protected exclusively, by the t-butyloxycarbonyl group. The side-chain protecting group which were used were 2-Br-Z (Tyr), 2,6-Cl₂-Bzl (Tyr), Tos (Arg, 2-Cl-Z (Lys), Bzl (Glu), and Z (<Glu). The following tlc systems were used: $R_f^1$, N-BuOH:EtOAc:AcOH:H₂O(1:1:1:1); $R_f^2$, EtOAc:Py:AcOH:H₂O(5:5:1:3) $R_f^3$, n-BuOH:-Py:AcOH:H₂O(30:20:6:24); $R_f^4$, 2-Propanol:1N AcOH(2:1); $R_f^5$, CHCl₃: conc. NH₄OH:-MeOH(60:20:45); $R_f^6$, Py:AcOH:H₂O(50:30:15).

Boc-Leu-Resin Ester.

The Merrifield resin (2.1 g) was suspended in 30 ml of ethanol. A solution of 0.70 g (2.71 mM) of Boc-Leu and 0.9 equivalent of Et₃N (2.43 mM, 0.34 ml) in 3 ml of ethanol was added to the resin suspension. The mixture was stirred slowly at 90° C. under anhydrous conditions for 24 hours using a magnetic stirrer. The esterified resin was washed successively with EtOH, H₂O, MeOH and CH₂Cl₂; floated 3 times with CH₂Cl₂ to get rid of fine resin particles; and dried in vacuo over P₂O₅. Amino acid analysis gave a value of 0.25 mM of Leu/g of substituted resin.

Boc-Asn-Lys(2-Cl-Z)-Pro-Arg(Tos)-Arg(Tos)-Pro-Tyr(2,6-Cl$_2$-Bzl)-Ile-Leu-CH$_2$-Resin Boc-Leu-resin ester (0.25 mM of Leu/g of Merrifield resin, 2.39 g) was added to the reaction vessel and after deprotection and neutralization, eight Boc-protected amino acid derivatives were successively coupled by the procedure described above to give the protected nonapeptide resin. This material was divided into two parts, one for neurotensin, another for its analog (Gln$^4$)-NT.

Neurotensin;
<Glu-Leu-Tyr-Glu-Asn-Lys-Pro-Arg-Arg-Pro-Tyr-Ile-Leu-OH.

The nonapeptide-resin ester was taken through another four cycles of deprotection, neutralization and coupling with the following amino acid derivatives: Boc-Glu(OBzl), Boc-Tyr(2,6-Cl$_2$-Bzl), Boc-Leu, and Z-<Glu to give the protected tridecapeptide resin by the methods described above. The protected tridecapeptide resin was cleaved and deprotected by anhydrous HF. The crude lyophilized product was subjected to partition chromatography on a 2 × 100 cm column of Sephadex G-25, eluted with the system n-BuOH:AcOH:H$_2$O(4:1:5) with detection of the peptide peaks by UV at 280 nm. The main fraction (196 mg) was chromatographed on a 1.5 × 100 cm Sephadex LH-20 column, eluted with n-BuOH:H$_2$O (6:100) with detection of the peptide peaks by UV at 280 nm giving 157.6 mg of partially purified neurotensin. This product was further purified on a 1.5 × 30 cm CM-52 ion exchange column, eluted with a gradient buffer solution of NH$_4$OAc (from 20 mM to 100 mM) to give neurotensin, 125 mg). Amino acid analyses gave the following ratios: Glu 1.07 × 2, Leu 1.00 × 2, Tyr 1.00 × 2, Asp 0.93, Lys 0.94, Pro 1.05 × 2, Arg 1.06 × 2, Ile 0.80. The tlc values were: R$_f^1$ 0.60; R$_f^2$ 0.87; R$_f^3$ 0.53; R$_f^4$ 0.51; R$_f^5$ 0.35; R$_f^6$ 0.98; each a single spot with the Pauly, I$_2$, and chlorine, o-tolidine reagents. There was only one component, moving toward the cathode, in paper electrophoresis in pyridine acetate buffer of pH 3.6 (and by the same detecting reagents). Neurotensin showed a specific rotation of $[\alpha]_D^{22.5}$ −90.42° (0.71, 1% AcOH).

<Glu-Leu-Tyr-Gln-Asn-Lys-Pro-Arg-Arg-Pro-Tyr-Ile-Leu-OH (Gln$^4$)-NT

This peptide was synthesized from the nonapeptide-resin ester, in an analogous fashion to neurotensin, except for the use of Boc-Gln-ONP in the coupling step on the first cycle. The protected tridecapeptide resin was cleaved and deprotected by anhydrous HF. The crude lyophilized product was subjected to partition chromatography on a 2 × 100 cm column of Sephadex G-25, eluted with the system n-BuOH:AcOH:H$_2$O(4:1:5), with detection of the peptide peaks by UV at 280 nm. The main fraction (150 mg) was chromatographed on another Sephadex G-25 partition column, with the 4:1:5 system, to give 140 mg, which was further purified by a 1.5 × 30 cm CM-52 ion exchange column, with the NH$_4$OAc gradient (from 20 mM to 100 mM), to give 120 mg of peptide ([Gln$^4$]-NT).

Amino acid analyses gave the following ratios: Glu 1.05 × 2, Leu 1.02 × 2, Tyr 1.01 × 2, Asp 1.07, Lys 0.91, Pro 0.99 × 2, Arg 1.00 × 2, Ile 0.86. The tlc values were: R$_f^1$ 0.27; R$_f^2$ 0.87; R$_f^3$ 0.51; R$_f^4$ 0.43; R$_f^5$ 0.20; R$_f^6$ 0.98; each a single spot with the Pauly, I$_2$ and chlorine, o-tolidine reagents. Only one component, moving toward the cathode, was observed on paper electrophoresis. The analog (Gln$^4$-NT) showed a specific rotation of $[\alpha]_D^{22.5}$ −86.20° (0.65, 1% AcOH).

These described syntheses yielded neurotensin, designated as NT, and [Gln$^4$]-neurotensin designated as [Gln$^4$]-NT. The activities of neurotensin and [Gln$^4$]-NT are summarized in the following table.

Table 1.

| Hypotensive Assay | | | |
|---|---|---|---|
| Peptide | Dose picomoles/100 g body weight | | −ΔSystemic (mm HG) Blood Pressure |
| NT (Neurotensin) | 50 | | 45 ± 5 (4) |
| [Gln$^4$]-Neurotensin | 50 | | 42 ± 8 (4) |
| Hyperglycemic Assay | | | |
| Peptide | Dose picomoles/100 g body weight | | |
| | 25 | 50 | 100 |
| NT | 18±5 mg %(3) | 36±4 mg %(4) | 97 (2) |
| [Gln$^4$]-NT | 15±5 mg %(4) | 34±4 mg %(4) | 116 (2) |
| Contraction of Guinea Pig Ileum | | | |
| Peptide | | | |
| NT and [Gln$^4$]-NT | about equivalent potency | | |
| Radioimmunoassay | | | |
| Peptide | 11/30 % Cross Ractivity (Ab #4, #6) | | |
| NT and [Gln$^4$]-NT: | 90–100% | | |

These assays for the activities of neurotensin and [Gln$^4$]-NT were conducted as follows.

Hypotensive Assay

Systemic blood pressure was measured with a Hewlett-Packard recorder and pressure transducer (preamplifier 8805 B, recorder 7782 A, transducer 267 BC) following cannulations of the carotid artery in rats weighing 200–250 g and anesthetized with pentobarbital (50 mg/kg). The test samples were dissolved in 0.85% saline and administered via a tail vein. The number of rats tested are given in parenthesis. The data are in Table 1.

Hyperglycemic Activity

Rats weighing 100–125 g were anesthetized with pentobarbital (50 mg/kg). The test samples were dissolved in 0.85% saline and administered via a tail vein. Each animal was killed by decapitation 15 minutes after injection and plasma glucose levels were measured by the method of Ceriotti and Frank. The number of rats tested are given in parenthesis. The plasma glucose values are given in mg %. The data are in Table 1.

Contraction of Guinea Pig Ileum

Freshly dissected segments of guinea pig ileum were suspended in a 40 ml bath which was maintained at 37° and serated with a mixture of $O_2$—$CO_2$ (95:5), and containing Tyrode's solution. The data are in Table 1.

Radioimmunoassay

A highly sensitive radioimmunoassay of Carraway and Leeman (The amino acid sequence, chemical synthesis and radioimmunoassay of neurotensin. Fed. Proc. 33, 548 (1974)) has been developed which utilizes $I^{125}$ labelled synthetic NT and rabbit antisera raised toward synthetic NT conjugated with poly-glutamic acid (60%) lysine (40%). Two antisera were used in these assays. One has been characterized as being directed solely toward the COOH-terminus, and the other requires most of the molecule.

The radioimmunoassay method used was an equilibrium system carried out at pH 7.4 in 10 × 75 mm disposable flint glass tubes and employing PBS-gel as diluent. The 500 μl incubation mixtures contained 100 μl of diluted rabbit anti-NT serum, 100 μl of $I^{125}$-NT containing ca. 15,000 cpm, and 100 μl of standard synthetic NT or of the analog. The mixtures were allowed to stand at 4° C. for 18–24 hours. The "bound" (B) and "free" (F) trace were separated at 4° C. by the rapid addition of 1.0 ml of a 1:4 dilution of a stock suspension of charcoal (2.5%) and dextran T-70 (0.25%) in PBS to each tube. The tubes were immediately centrifuged for 20 min at 2000 rpm (PRJ-Universal), and the supernatant fluids were decanted into new tubes. Both the supernatant (B) and the sedimented characoal (F) were counted in an automatic gamma scintillation counter for 1 min and B/F were corrected for "damaged" trace by subtracting the B/F observed for the appropriate sample in the absence of antibody. "Damage" was usually 2–4% and using antisera at a final dilution of 1:10,000 gave 50–70% binding. All unknowns were assayed in duplicate at three dilutions so as to span the sensitive portion of the curve. The results were obtained by averaging the concentrations determined at each dilution provided that they agreed within 20%. The data are in Table 1.

[Gln$^4$]-neurotensin ([Gln]$^4$-NT) has also been studied on the heart and on the blood from in subcutaneous adipose tissue, skin, and small intestine in anesthetized dogs. In addition, its possible action has been investigated on blood glucose concentration and lypolysis in subcutaneous adipose tissue. [Gln]$^4$-NT was found to show both vasodilator and vasoconstrictor actions in the peripheral vasculature, but no cardiac action. It also increased blood glucose concentration.

[Gln]$^4$-NT is useful to produce at the mammalian level including man a decrease in blood pressure and an increase in intestinal blood flow. The control of essential hypertension or elevated blood pressure in man is one of the most serious diseases. [Gln]$^4$-NT is also useful to inhibit gastric acid secretion, under conditions which caused no direct actions on the heart and no evidence of a change in lipid metabolism in adipose tissue. [Gln]$^4$-NT has a useful cardiovascular profile which is quite different from that of Substance P, which is another polypeptide extracted from the hypothalamus. Substance P induced hypotension and pronounced vasodilation and no vasoconstrictor or metabolic actions. [Gln$^4$]-NT produces a useful delayed vasoconstriction which is prominent is subcutaneous adipose tissue, which is of particular value.

The synthetic tridecapeptide, [Gln$^4$]-neurotensin, is useful to benefit medical patients with a penetrating peptic ulcer. Such patients are in an acute clinical situation. At the present time, such patients are treated with anti-acids and gastric suction. These current treatments are unsatisfactory and may be considered "crude". The use of this new tridecapeptide would be a specific hormonal treatment and be a substance which has unique and intrinsic potency and activities. This tridecapeptide, [Gln$^4$]-neurotensin, can intravenously block the production of hydrochloric acid in the stomach and inhibit the mobility of the stomach and duodenum. This new tridecapeptide, [Gln$^4$]-neurotensin, is also useful because of its unique hormone-like activites, to increase the peristaltic movements of the lower part of the small intestine. Because of this effect, this substance is uniquely suitable to induce a normal postsurgical peristalsis in patients. Today, all patients in hospitals undergoing abdominal surgery have problems with an atonic intestine for 3–4 days after surgery. This atonic intestine can be stimulated to normal peristalsis by appropriate treatment of such patients with this new tridecapeptide and relieve a highly undesirable post surgical abdominal situation which is contrary to the recovery of such patients.

CRITIQUE OF THE ISOLATION OF NEUROTENSIN BY CARRAWAY AND LEEMAN

The isolation of neurotensin from bovine hypothalami was described by Carraway and Leeman (J. Biochem. 248, 684–6861 (1973)). It was read on page 6856 that the frozen tissue (usually 20–45 kg) was homogenized to uniform consistency at $-20°$ with an equal volume of acetone-1N HCl (100:3 v/v) in a colloid mill; then three more volumes of this solvent were added, and the suspension was stirred overnight at 4°. The mixture was filtered, and the filtrate was set aside. The residue from the filtration was resuspended in a volume of acetone 0.01 N HCl (80:20 v/v) that was 3-times the orignal volume of the tissue. The mixture was filtered. The two filtrates were pooled. Repetitive petroleum ether extraction of the combined filtrates removed lipid as well as acetone, and was accomplished as follows: The filtrate was mixed at 4° with one-third of its volume of petroleum ether; the ether-acetone phase was discarded, and the process was repeated 3–4 times until the discarded phase was transparent. The acetone-water phase was then evaporated under reduced pressure at water bath temperature of 35°–45° (THE TEMPERATURE OF 35°–45° FOR THIS LYOPHILIZATION WAS QUESTIONED), to remove acetone, and the aqueous residue was finally lyophilized. The extraction and initial fractionation steps on a preparative scale were performed at the New England Enzyme Center in Boston (PREPARATIVE SCALE EXTRACTION UTILIZING A TEMPERATURE OF 35°–45° FOR LYOPHILIZATION WAS ALSO QUESTIONED. IN ADDITION, THE USE OF 1 N HCl AND 0.01 N HCl IN SUCCESSIVE STEPS WAS ALSO QUESTIONED).

Fractionation of the extract was next performed in two successive steps on a 20-liter and a 5-liter column of Sephadex G-25. The lyophilized extract was taken up in 0.1 M acetic acid (600 ml/22kg of hypothalami), and after its pH was adjusted to 4, the suspension was centrifuged at 10,000 g for 20 min at 4° C.

The supernatant was resuspended in solvent and recentifuged on the basis of 400 ml/20 kg of hypothalami. The recombined supernatant fluid was then applied to a 20-1 column of Sephadex G-25 which was equilabrated with 0.1 M acetic acid at 4°.

EXPERIMENTAL TESTS OF CONCEPTION ON THE ARTIFACTUAL NATURE OF NEUROTENSIN

The inventor of this application questioned whether the tedious and time-consuming isolation of neurotensin by Carraway and Leeman could have inadvertently allowed the hydrolysis of a [Gln$^4$]-moiety, if this moiety were actually present in the peptide hormone as it exists in the bovine hypothalamus. Consequently, neurotensin and its three acid and amide analogs, i.e., [Gln$^4$]-neurotensin, neurotensin-NH$_2$, and [Gln$^4$]-neurotensin-NH$_2$ were synthesized, Neurotensin and [Gln$^4$]-neurotensin were similar by hypertensive assay, hyperglycemic assay, contraction of the ileum and radioimmunoassay.

Other experiments were conducted to test the conception of the artifactual nature of neurotensin and of the possible natural occurrence of [Gln$^4$]-neurotensin in the hypothalamus.

The basis of the original conception about the possible natural occurrence of [Gln$^4$]-neurotensin was based on the knowledge that the initial extraction of the tissue, as described by Carraway and Leeman, was relatively large in quantity — "usually 20–45 kg " — and after a few preliminary steps, there was an acetone-water phase which — "was then evaporated under reduced pressure (water bath temperature 35°–45°) to remove acetone, and the aqueous residue was finally lyophilized". This evaporation at 35°–45° was presumed to have required many hours, because it was performed on a preparative scale — at the New England Enzyme Center in Boston.

The conception that neurotensin might be an artifact was substantially based upon the "suspect step" of evaporation at 35°–45° during the isolation procedure, and also upon other "suspect steps" including the ones where the frozen tissue (20–45 kg) was homogenized with an equal volume of acetone1 N HCl (100:3 v/v). Subsequently, evaporation at 35°–45° took place.

Toward simulation of these isolation steps, both in terms of temperature and the concentration of hydrochloric acid, 2 mg of synthetic [Gln$^4$]-neurotensin was dissolved in a mixture of acetone 1 N HCl (100:3 v/v), and this solution was maintained at 37° C. for 12 hours which can be presumed to be less than the time of the original large scale operation at the New England Enzyme Center in Boston. An aliquot of the solution was taken for thin layer electrophoresis on cellulose plates (160 microns, Eastman Chromatographic sheet) at 500 volts in pyridine-acetate buffer, pH 6.5. The major spot on the plate corresponded to [Gln$^4$]-neurotensin. However, a new and minor spot moving toward the cathode was present which had the same TLC retention time as neurotensin. The solution was allowed to stand overnight, and it was then maintained again at 37° for a second 12-hr period. The electrophoresis of another aliquot showed the same two spots, but now with about the same intensities by the ninhydrin and chlorine o-tolidine color tests. The minor spot had increased during the second 12-hr period. The remaining solution was concentrated under reduced pressure at room temperature to remove acetone, and the aqueous residue was then lyophilized. The residual white powder was subjected to thin layer electrophoresis on cellulose plates and pyridine acetate buffer at pH 6.5 and at 500 volts. About 1 mg of [Gln$^4$]-neurotensin was recovered, which on subsequent tlc analysis revealed a single spot with the Pauly, ninhydrin, and chlorine o-tolidine reagents. The $R_f$ values were identical with those of an authentic specimen of [Gln$^4$]-neurotensin as follows: $R_f^1$ 0.25; $R_f^2$ 0.89; $R_f^3$ 0.50; $R_f^4$ 0.42; $R_f^5$ 0.21; and $R_f^6$ 0.98.

The following tlc systems were used: $R_f^1$, n-BuOH:EtOAc:AcOH:H$_2$O (1:1:1:1); $R_f^2$, EtOAC:Py:AcOH:H$_2$O (5:5:1:3); $R_f^3$, n-BuOH:Py-AcOH:H$_2$O (30:20:6:24); $R_f^4$, 2-propanol:1NAcOH (2:1); $R_f^5$, CHCl$_3$:conc, NH$_4$OH:MeOH (60:20:45); $R_f^6$, Py:AcOH:H$_2$O (50:30:15).

The new band, moving toward the cathode was recovered and found to amount to about 1 mg. This material on subsequent tlc analysis behaved as a single spot according to the Pauly, ninhydrin, and chlorine o-tolidine reagents. The $R_f$ values were as follows: $R_f^1$ 0.59; $R_f^2$ 0.87; $R_f^3$ 0.52; $R_f^4$ 0.51; $R_f^5$ 0.36; and $R_f^6$ 0.98. These $R_f$ values are identical with those of authentic neurotensin.

This experiment demonstrated that synthetic [Gln$^4$]-neurotensin was hydrolyzed or converted to neurotensin under the conditions of procedure used by Carraway and Leeman for the processing of the hypothalamic tissue. Because of the importance of this experiment, and the conclusion, the experiment was repeated and on a larger scale.

In the second experiment 10 mg of pure [Gln$^4$]-neurotensin was dissolved in a mixture of acetone 1 N HCl (100:3 v/v), and the solution was maintained at 37° C. for 27 hours to simulate again the steps of isolation which are being critiqued. This time, 3 spots were observed on electrophoretic analysis of an aliquot of the solution which had been maintained at 37° for 27 hrs. Preparative thin layer electrophoresis, extraction, and workup yielded 4.2 mg of recovered [Gln$^4$]-neurotensin and 4.3 mg of neurotensin. The third and much weaker spot was due to only a trace amount of another peptide which presumably resulted from further hydrolysis. This third spot or peptide is not important to the second experiment which demonstrated again that conditions used in the isolation of neurotensin from hypothalamic tissue actually does convert [Gln$^4$]-neurotensin to neurotensin. The fact that in these two experiments, not all of the [Gln$^4$]-neurotensin was converted to neurotensin is relatively unimportant, because these experiments on hydrolysis of the pure [Gln$^4$]-neurotensin only simulates the conditions of processing of 20–45 kg of hypothalamic tissue. However, these two experiments do prove that steps used in the isolation by Carraway and Leeman do convert or hydrolyze [Gln$^4$]-neurotensin to neurotensin.

FURTHER DATA ON THE PHYSIOLOGICAL IMPORTANCE OF [Gln$^4$]-NEUROTENSIN

The action of [Gln$^4$]-neurotensin was tested on the spontaneous motor activity in isolated canine fundic, antral and intestinal pouches. All of these pouches had been prepared more than 6 months prior to the testing. Spontaneous motor activity was observed for at least 1 hour before the [Gln$^4$]-neurotensin was infused intravenously for 30 min in doses ranging between 6.3 and 100 ng $\times$ kg$^{-1}$ $\times$ min$^{-1}$. In the vagally denervated fundic pouches [Gln$^4$]-neurotensin was observed to inhibit motor activity in doses above 25 ng $\times$ kg$^{-1}$ $\times$ min$^{-1}$. The vagally innervated antral pouches were found to be more sensitive than the vagally denervated fundic pouches to the action of [Gln$^4$]-neurotensin. Significantly motor inhibition was induced by doses as low as 6.3 ng $\times$ kg$^{-1}$ $\times$ min$^{-1}$. These results showed that the gastric motor activity is a highly sensitive function to [Gln$^4$]-neurotensin. The gastro-intestinal tract appears to be the principal target organ for [Gln$^4$]-neurotensin, and is a basis for clinical use of [Gln$^4$]-neurotensin in patients having diseases of gastroenterology (S. Andersson, M.D. S. Rosell M.D., U. Hjelmquist M.D., D. Chang Ph.D. and K. Folkers Ph.D., *Gastroenterology*, in press).

IMPORTANCE OF [Gln$^4$]-NEUROTENSIN OVER NEUROTENSIN WHICH HAS NOW BEEN FOUND TO BE AN ARTIFACT OF ISOLATION

In mammalin endocrinology, it is important to identify and know the native peptide hormone as it exists in given mammalian tissue such as the hypothalamus. The native peptide hormone can be the peptide of choice for use either in veterinary medicine or in human medicine, as the case may be.

The difference in the structure and conformation between [Gln$^4$]-neurotensin and neurotensin can be very significant, because the [Gln$^4$]-moiety is "neutral" and the [Gln$^4$]-moiety is acidic. The presently known bioassays in laboratories of pharmacology on neurotensin, etc., only revealed activites under the laboratory determined conditions and these activities may not completely reflect the behavior and function of the native hormone in the mammalian body. It is to be expected that [Gln$^4$]-neurotensin is superior to neurotensin in certain biological details.

[Gln$^4$]-neurotensin is superior to neurotensin for use in mammalian physiology or in veterinary or human medicine, because it is the native peptide hormone having specific mammalian functions.

EXAMPLE OF SYNTHESIS

The example set forth in this document is an effective and useful synthesis of the importnat [Gln$^4$]-neurotensin which has the useful physiological activities of an intrinsic or native hormone.

What is claimed:

1. A synthetic tridecapeptide having the structure pGlu-Leu-Tyr-Gln-Asn-Lys-Pro-Arg-Arg-Pro-Tyr-Ile-Leu-OH wherein all 13 amino acids are of the L-configuration.

* * * * *